(12) United States Patent
Ellman et al.

(10) Patent No.: US 6,395,002 B1
(45) Date of Patent: May 28, 2002

(54) ELECTROSURGICAL INSTRUMENT FOR EAR SURGERY

(76) Inventors: Alan G. Ellman; Jon C. Garito, both of 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 09/483,993

(22) Filed: Jan. 18, 2000

(51) Int. Cl.[7] .............................................. A61B 18/18
(52) U.S. Cl. .......................................... 606/45; 606/48
(58) Field of Search ............................. 606/34, 37, 39, 606/40, 41, 42, 43, 44, 45, 46, 47, 48, 49, 50, 110, 113, 162; 607/137

(56) References Cited

U.S. PATENT DOCUMENTS 5,403,311 A * 4/1995 Abele et al. .................. 606/49
5,741,250 A * 4/1998 Garito et al. .................. 606/45
5,925,045 A * 7/1999 Reimels ...................... 606/48

* cited by examiner

*Primary Examiner*—R. Kearney

(57) ABSTRACT

An electrode for use in an electrosurgical aural procedure known as a myringotomy for removing tissue of the tympanic membrane. In a preferred embodiment, the electrode is characterized by a bare active end portion that is hollow and has an outside diameter of 2–3 mm. In a unipolar embodiment, the bare end has a sharp circular edge; in a bipolar embodiment, the bare end is split into two semi-circular sharp edges that may be axially offset from one another. When the electrode end is placed against the tympanic membrane and the electrosurgical apparatus activated, a 2–3 mm hole is punched in the tympanic membrane which allows any middle ear fluid to drain.

6 Claims, 3 Drawing Sheets

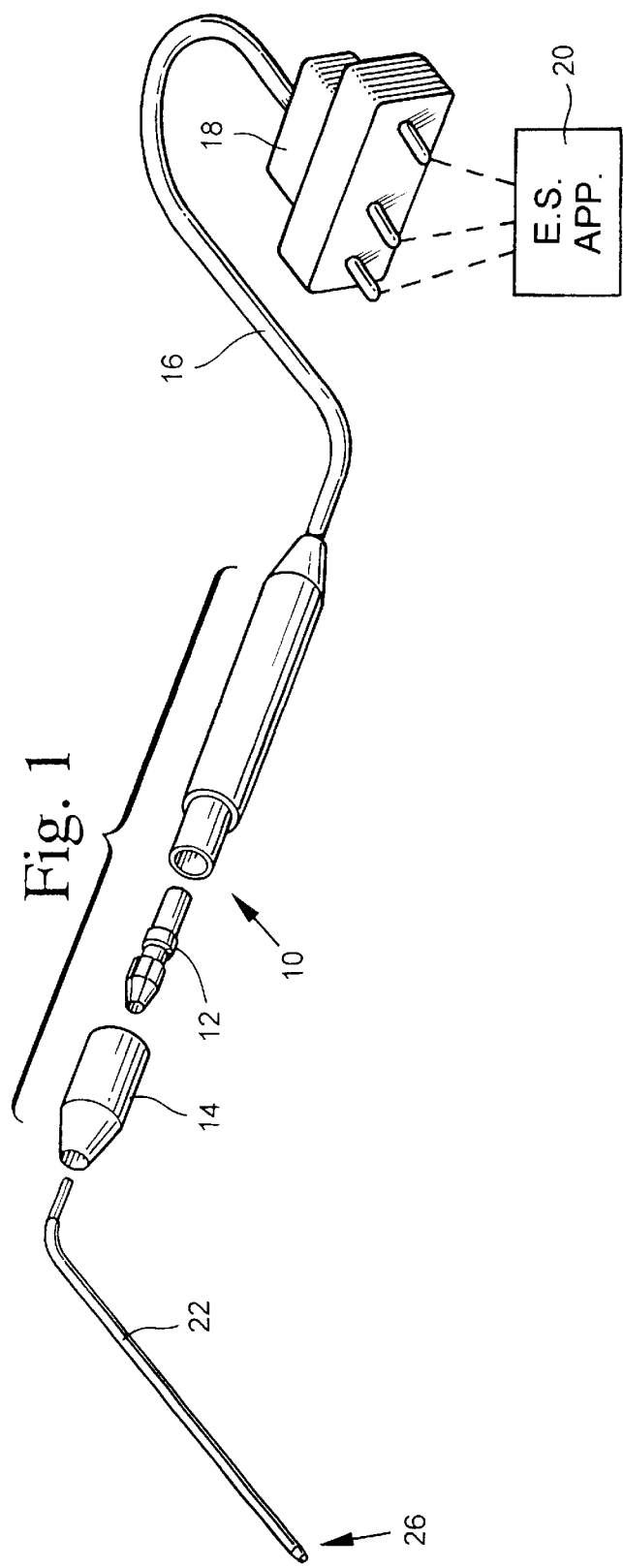

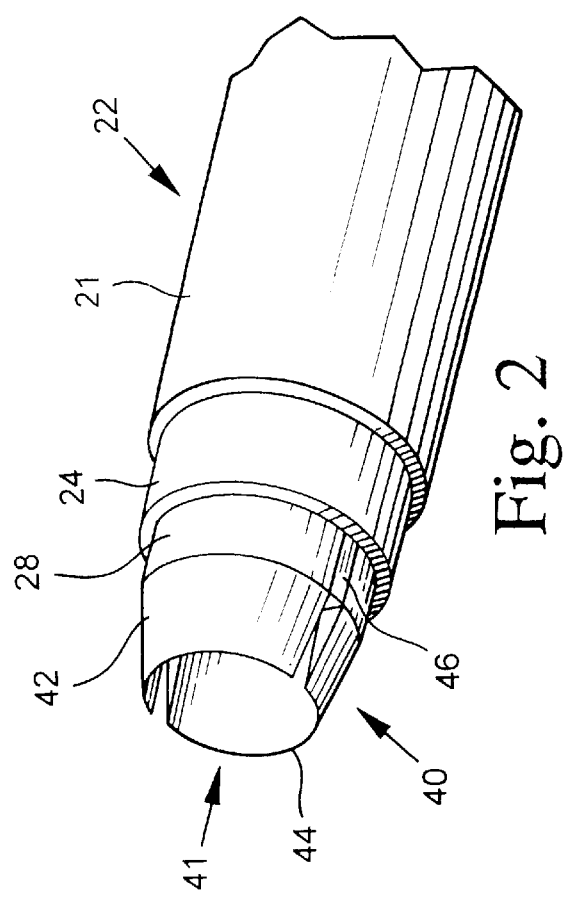
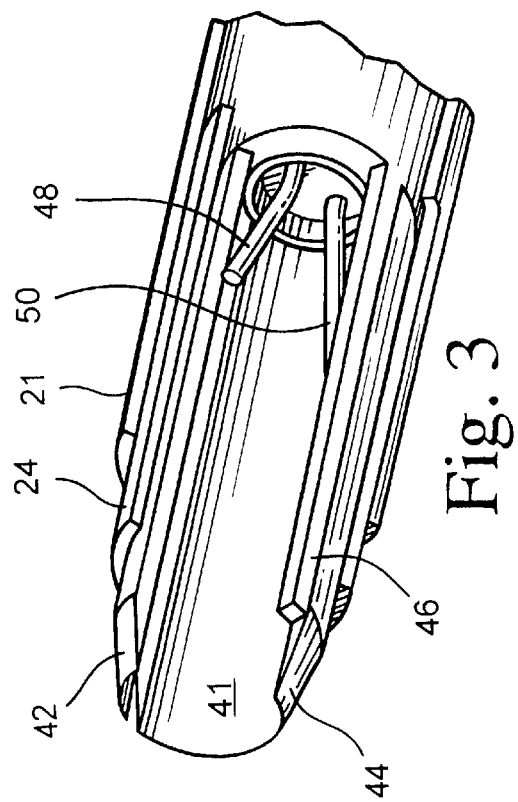

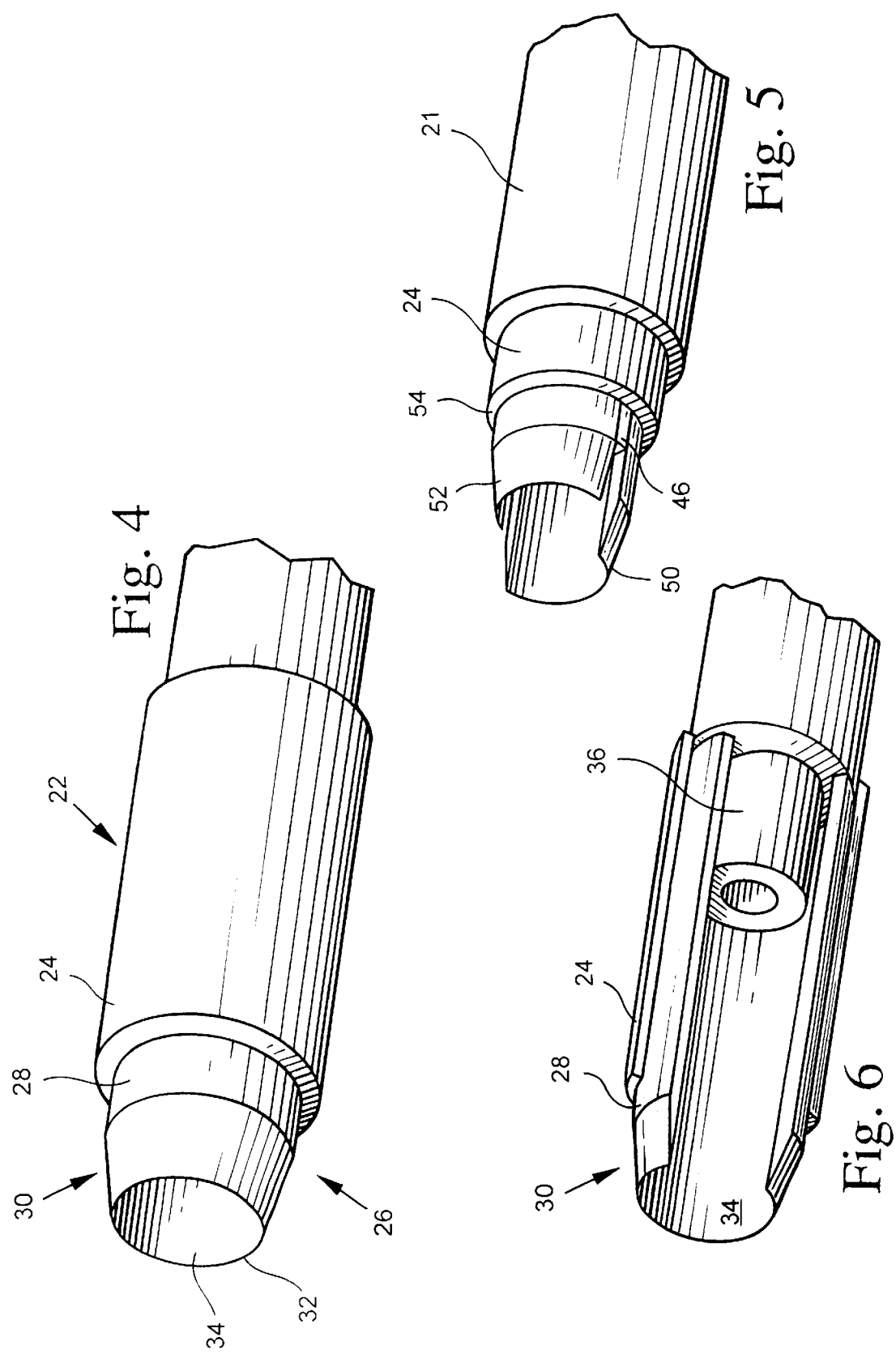

ELECTROSURGICAL INSTRUMENT FOR EAR SURGERY

RELATED APPLICATION

U.S. application, Ser. No. 09/435,677, filed Nov. 8 1999, commonly owned, for "Electrosurgical Instrument for Ear Surgery", of which the present application is a continuation-in-part.

This invention relates to an electrosurgical instrument for ear surgery, and in particular, for use in a myringotomy procedure.

BACKGROUND OF THE INVENTION

Reference is made to our prior issued patent No. 5,741,250, whose contents are incorporated herein by reference. This prior patent describes an improved myringotomy surgical procedure involving an incision of the tympanic membrane that is made to allow ventilation of the middle ear, to permit drainage of middle ear fluid, or to obtain cultures from an infected middle ear. The improved procedure uses a solid wire electrode and electrosurgical apparatus to form the hole in the tympanic membrane. The electrosurgical procedure has the important advantage of being able to cut the tissue while at the same time coagulating the cut tissue causing minimum bleeding. The structure of the novel electrode described in the prior patent used to make the incision prevents the excision depth from exceeding a safe value. In accordance with another feature of that invention, the electrode is uniquely configured to enable the active tip to reach the tympanic membrane via the ear canal passageway and incise the desired tissue while avoiding damage to surrounding tissue.

Recently, a new treatment called OtoScan Laser Assisted Myringotomy (OtoLAM) has been described. It uses a $CO_2$ laser to vaporize an allegedly precisely sized preset hole in the tympanic membrane without damaging surrounding structures. The preset hole remains open for several weeks allowing ventilation of the middle ear and avoiding the need for grommets to keep the hole open until the middle ear region is adequately drained. The main disadvantage of this procedure is the use of a highly expensive laser instrument requiring training for those physicians that are not familiar with such equipment.

Our prior filed patent application, Ser. No. 09/435,677, whose contents are incorporated herein by reference, describes an improved electrode for a myringotomy surgical procedure comprising a hollow tube with a sharpened edge or a conically pointed electrode dimensioned to produce a desired hole size.

SUMMARY OF THE INVENTION

The present invention is a continuation-in-part of the prior application and hereby incorporates by reference the total contents of the prior application. The present invention describes several additional electrodes for use in a myringotomy surgical procedure but otherwise makes use of the same teachings of the prior application, and for this reason it was felt unnecessary to repeat in the body of this specification the total contents of the prior application. The present description will be confined solely to the differences in the electrode ends to achieve certain benefits that may be more difficult to achieve with the electrode constructions of the prior application.

SUMMARY OF THE INVENTION

An object of the invention is an improved myringotomy surgical procedure.

We have invented a novel electrode for use in an electrosurgical myringotomy procedure. This electrosurgical procedure using our novel electrode enables physicians to offer to patients a treatment that is efficiently performed, easily learned and thus performed at a significantly reduced price, and with less tissue damage and bleeding compared to procedures done with a knife or needle.

The procedure using our novel electrosurgical electrode is based on forming a hole in the tympanic membrane, preferably of approximately 2–3 mm in size, which is large enough to allow adequate drainage from the middle ear over several weeks, but not too large so as to delay healing.

In a first preferred embodiment, a bipolar electrode is used with a split electrode end that is hollow and is provided with a circular knife edge whose outer diameter is approximately 2–3 mm. The two halves of the split hollow end are insulated from one another allowing an electrosurgical voltage to be applied between them capable of causing a discharge of electrosurgical currents capable of puncturing a hole in the tympanic membrane. The cutting edges of the two halves lie in a common plane. In a second preferred embodiment, the cutting edges of the two insulated halves are axially offset from one another. In both cases, the surgeon places the electrode end against the tympanic membrane and activates the electrosurgical apparatus. The result is to punch a hole in the membrane, by the flow of electrosurgical currents between the insulated halves, that is of the same size as the outer diameter of the electrode end.

In comparison with the laser procedure, the electrosurgical equipment is far less expensive and many physicians are already trained in the use of electrosurgical apparatus. Moreover, for those untrained, the training procedure is relatively simple and consumes little time.

Another preferred embodiment of the invention is a unipolar electrode with a circular knife edge that is bare and tapered extending from an insulated section to inhibit the flow of electrosurgical currents. A thicker insulated section can serve as a stop. The insulated sections can be color-coded to indicate to the practitioner the depth of penetration of the electrode.

In accordance with another feature of the invention, the interior of the hollow electrode end is provided with a stop which will allow severed tissue to remain inside the hollow electrode allowing its easy removal and disposal by the surgeon.

As described in the prior patent, the electrode of the invention is also configured to enable the active tip to reach the tympanic membrane via the ear canal passageway and punch the desired tissue hole while avoiding damage to surrounding tissue.

In a preferred embodiment, our novel electrode is characterized by a straight electrically-insulating portion extending from an insulated handle and terminating in an active bare hollow end portion. The incision is effected with the bare hollow end moved by the surgeon in a generally straight path, and the adjacent portions of the hollow end support and electrode shaft are made insulating to prevent accidental burns to the patient and to allow the physician to use these insulated parts to help position and guide the active tip portion during the surgical procedure. The electrosurgical procedure has the important advantage of being able to punch the tissue while at the same time coagulating the cut tissue causing minimum bleeding. It is preferred that the electrosurgical currents used be above 2 MHz, and preferably above 3 MHz. At these high frequencies, commonly referred to as radiosurgery, cutting is accomplished by volatilizing intracellular fluids at the point of the transmitting electrode contact which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

BRIEF DESCRIPTION OF THE DRAWINGS

In the drawings:

FIG. 1 is a perspective, partly exploded view of a first unipolar embodiment of an electrosurgical myringotomy punch electrode in accordance with the invention, shown connected to electrosurgical apparatus;

FIG. 2 is a perspective view of the working end of a second bipolar embodiment of an electrosurgical myringotomy punch electrode in accordance with the invention;

FIG. 3 is a view of the working end of the electrode of FIG. 2 with part of it cut away to show the interior;

FIG. 4 is a perspective view of a third unipolar embodiment of an electrosurgical myringotomy punch electrode in accordance with the invention;

FIG. 5 is a perspective view of the working end of a fourth embodiment of an electrosurgical myringotomy punch electrode in accordance with the invention;

FIG. 6 is a partial cross-sectional view of the working end of a fifth embodiment of an electrosurgical myringotomy punch electrode in accordance with the invention.

DETAILED DESCRIPTION OF THE PREFERRED EMBODIMENTS

FIG. 1 illustrates a first preferred form of a unipolar electrosurgical myringotomy punch electrode 10 of the invention. It comprises a handpiece 10 comprising a collet 12, a nosepiece 14, and a cable 16 connected to the handpiece whose other end is connected via a connector 18 to electrosurgical apparatus 20. Alternatively, a handle of electrically-insulating material made up of separable parts that allows separation of the handle to permit insertion of another form of myringotomy punch electrode as shown in FIG. 1 of the prior pending application can be used. As an example only, the electrosurgical apparatus 20 can be Model Dual Frequency Surgitron available from Ellman International, Inc. of Hewlett, N.Y. The Ellman equipment is preferred due to its high operating frequency, typically above 2 MHz, preferably at 3.8–4.0 MHz.

The electrode 22 itself comprises a bent elongated inner metal tube 23 covered with electrically-insulating material 24, for example, a heat-shrunk plastic tube. The outer layer 21 may be of metal. In operation, a bare end of the tube 23 is mounted through the nosepiece 14 in the collet 12 which is electrically-connected to the cable 16. The portion 26 (FIG. 4) of the tube 22 projecting from the end of the electrically-insulating tube 24 is coated with a thin electrically-insulating coating 28, except for a short bare part 30 terminating in a circular sharp edge 32 surrounding a center bore 34 having a longitudinal axis (horizontal in FIG. 4). The sharp edge 32 which is bare serves as the working end of the electrode. Also connected to the electrosurgical apparatus 20 is the usual indifferent plate (not shown) which during use is in contact with a patient's body. When the electrosurgical apparatus 20 is energized, high frequency electrosurgical currents are generated which are coupled by way of the cable 16 and electrically-conductive tube 23 to the active, bare end 30. The physician, in the usual way, holds the handpiece 10 while applying the active working end 26 of the electrode to the desired area of the patient to be treated.

In the unipolar version depicted in FIG. 4, the bare active end 30 has a long taper, for example, about 0.035–0.05 inches long, preferably about 0.04 inches long from the edge of the thin insulator 28 to the knife edge 32. The taper defines a cone angle that can vary between about 10° and 20°. Limiting the length of the active bare end 30 to 0.035–0.05 inches ensures that the electrode will complete the incision process so long as it is pushed in until the thin insulator 28 is reached. This can be of assistance to the surgeon by coloring the thin insulator 28 differently than the bare end 30, so that a clear visual indication is made available to the surgeon. Locating the thicker insulating tube 24 about 2 mm from the knife edge 32 allows the facing edge of the thicker tube to act as a stop to limit the penetration to 2 mm. The surgeon may at times find it necessary to advance the electrode end 30 up to about 70 mm, for certain thicknesses of the tympanic membrane, to ensure that the hole has completely penetrated the membrane. In that case, locating the thicker insulating tube 24 about 70 mm from the knife edge 32 allows the facing edge of the thicker tube to act as a stop. Similarly, the thicker tube 24 can be colored differently to provide a visual indication to the surgeon.

The electrically-insulating coating 28 together with the electrically-insulating tube 24 ensures that the only active part of the electrode is the short bare portion 30 in front thereby preventing inadvertent burns or other damage to other ear parts.

FIG. 6 shows a second embodiment of the unipolar electrode. The only difference is that a bored plug 36, which may be of plastic, is mounted in the bore 34. This acts to hold the severed tissue in place that allows easy removal and disposal of the tissue.

FIGS. 2, 3 and 5 disclose bipolar modifications. In this case, the handle or handpiece used would have to provide two electrically-insulated wire connections to the electrode so that an electrosurgical voltage can be applied between the two active bipolar ends. In the FIG. 2 variation, the metal tube 41, which is shorter, is split into two insulated halves, and the working end 40 comprises the same tapered end leading to a knife edge but now two semicircular knife edges 42, 44 air insulated in the tapered part and electrically-insulated by an insulator strip 46 throughout its length are present. FIG. 3 shows one possible way of accomplishing this in which two insulated wires 48, 50 coming from the connector 18 may be electrically attached, as by welding, to each of the tube halves 42, 44.

As before, when the electrosurgical apparatus 20 is activated, a bipolar electrosurgical voltage via the two insulated wires 48, 50 is applied across the two halves 42, 44. When their knife edges are pressed against the tympanic membrane, due to the discharge of electrosurgical currents between the two halves 42, 44, which are focused at the gap between the electrode halves, a hole will be punched in the membrane. To ensure a complete cut of the tissue, it may be desirable to rotate the handpiece over a small angle.

In the FIGS. 2 and 3 embodiment, the two split knife edges 42, 44 axially project about the same distance from the end of the insulating tube 24. In other words, the knife edges lie in a common plane transverse to the long axis of the electrode. In the embodiment of FIG. 5, the two split knife edges 50, 52 are axially offset and project different distances from the end 54 of the insulating tube 24. In this construction, when operated, the RF energy will focus at the longer knife edge 50, which first contacts the membrane. This will produce a more precise starting opening in the membrane. Continuing the inward pressure will produce the desired hole opening.

The thin insulating coating 28 may be, for example, of Teflon. The insulating strip 46 may be about 0.01 inch thick. The longer knife edge 50 may extend about 1–2 mm beyond the end of the shorter knife edge 52.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical bipolar electrode for punching a hole in the tympanic membrane of a patient, comprising;
    (a) an electrically-conductive member having a first end and a second end,
    (b) said second end having an active, electrically-conductive, end portion comprising a hollow tube terminating in a circular sharpened edge having a diameter of about 2–3 mm,
    (c) said active end portion being exposed electrically for applying electrosurgical currents to said tympanic membrane when the electrically-conductive member is connected to a source of electrosurgical currents,
    (d) portions of the electrically-conductive member adjacent said exposed end portion being electrically-insulating to prevent contact and passage of electrosurgical currents to tissue areas adjacent to or surrounding the hole to be punched,
    (e) the electrically-conductive member with its circular sharpened edge being split into two electrically-insulated semi-circular sharp edges, the electrosurgical currents being generated when an electrosurgical voltage is impressed across the two electrically-insulated semi-circular sharp edges,
    (f) whereby a 2–3 mm hole is punched in the tympanic membrane when the electrosurgical source is activated and the sharp edges of the electrode is placed against the tympanic membrane.

2. An electrosurgical electrode as claimed in claim 1, wherein the two electrically-insulated semi-circular sharp edges lie in a common plane extending transverse to a long axis of the electrode.

3. An electrosurgical electrode as claimed in claim 1, wherein the hollow tube comprises a long tapered section about 0.035–0.05 inches long terminating in the semi-circular sharp edges.

4. An electrosurgical electrode as claimed in claim 3, wherein the tapered section defines a cone angle that can vary between about 10° and 20°.

5. An electrosurgical electrode as claimed in claim 3, wherein the electrically-insulating portions comprise a thin insulated section adjacent the tapered section and a thicker insulated section whose edge is located about 2–70 mm from the sharpened edge and serves as a stop.

6. An electrosurgical electrode as claimed in claim 1, wherein the electrode has a long axis and the two electrically-insulated semi-circular sharp edges are axially offset from one another.

* * * * *